United States Patent [19]

Porteous

[11] 4,260,597

[45] Apr. 7, 1981

[54] THERMALLY REVERSIBLE DENTAL ASTRINGENT GELS

[76] Inventor: Don D. Porteous, 2794 Moraga Dr., Los Angeles, Calif. 90024

[21] Appl. No.: 72,704

[22] Filed: Sep. 4, 1979

Related U.S. Application Data

[63] Continuation-in-part of Ser. No. 944,274, Sep. 21, 1978, abandoned.

[51] Int. Cl.³ .............. A61K 7/16; A61K 31/74; A61K 33/06; A61K 31/19
[52] U.S. Cl. .............................. 424/49; 424/78; 424/154; 424/317; 424/343
[58] Field of Search ............ 424/78, 49, 154, 317, 424/343; 260/29.6 BN

[56] References Cited

U.S. PATENT DOCUMENTS

| | | | |
|---|---|---|---|
| 2,249,538 | 7/1941 | McDowell et al. | 260/29.6 BE |
| 2,408,377 | 10/1946 | Dangelmajer | 260/29.6 BM |
| 2,607,658 | 8/1952 | Govett et al. | 424/148 |
| 3,772,431 | 11/1973 | Mlkvy et al. | 424/49 |
| 3,856,941 | 12/1974 | Turner | 424/154 |

OTHER PUBLICATIONS

Remington's Pharm. Sci., 15 ed., (1975), 716-717.
Chem. Abst. 84, 65190(r), (1976), Turner.
Chem. Abst. 77, 52,375(k), (1972), Driessens.

*Primary Examiner*—Douglas W. Robinson
*Attorney, Agent, or Firm*—Donald Diamond

[57] ABSTRACT

Thermally reversible dental astringent gels are prepared by admixing and heating a fluid system containing substantially completely hydrolyzed polyvinyl alcohol of moderate molecular weight and moderate solution viscosity, polyhydroxy aromatic gelling agent such as gallic acid, aluminum chloride hydrate and water until a sample thereof, upon cooling, forms a solid, tack-free, elastomeric, thermally reversible gel.

21 Claims, No Drawings

THERMALLY REVERSIBLE DENTAL ASTRINGENT GELS

CROSS-REFERENCE TO RELATED APPLICATION

This application is a continuation-in-part of U.S. patent application Ser. No. 944,274, filed Sept. 21, 1978, and entitled Thermally Reversible Dental Astringent Gels, now abandoned.

BACKGROUND OF THE INVENTION

This invention relates to dental therapeutic compositions and, more particularly, to hemostatic dental astringents embodied in thermally reversible gels for treating gingival tissue.

In dental therapeutics, it is often necessary to retract and displace gingival tissue in order to prepare patients for taking impressions, setting crowns or effecting restorations.

Heretofore, gingival retraction was undertaken by mechanical means, electrosurgery or cutting away tissue as well as by application to the gingival crevice of a gingival retraction solution or a gingival retraction cord having a retraction solution absorbed onto its surface.

While the hemostatic/astringent solutions used in dental therapeutics are effective in retracting gingival tissue and useful in the control of local hemorrhage, nevertheless, these solutions have a drawback in that their flow characteristics are such that they stay on the tissue and are difficult to remove or that they run too rapidly and are carried away by saliva or moisture. Also, astringent soaked gingival retraction cord, when packed into the gingival sulcus, tends to slide outwardly from its packing position.

Accordingly, the principal object of this invention is to provide a thermally reversible gel system for applying hemostatic/astringent compositions to gingival tissue which permits these compositions to stay in place until the therapeutic purpose has been effected and thereafter permits the compositions to be readily and easily removed from the tissue.

SUMMARY OF THE INVENTION

In accordance with one aspect of this invention, there is provided a solid, tack-free, elastomeric, thermally reversible dental astringent gel composed of an admixture comprising substantially completely hydrolyzed polyvinyl alcohol of moderate molecular weight and moderate solution viscosity, polyhydroxy aromatic gelling agent, aluminum chloride and water.

In a second aspect of this invention, there is provided a method for preparing a thermally reversible dental astringent gel which comprising admixing and heating a fluid system containing substantially completely hydrolyzed polyvinyl alcohol of moderate molecular weight and moderate solution viscosity, polyhydroxy aromatic gelling agent, aluminum chloride and water until a sample thereof, upon cooling, forms a solid, tack-free, elastomeric, thermally reversible gel.

In a third aspect of this invention, there is provided a method for constricting and retracting gingival tissue and the like which comprises heating a solid, tack-free, elastomeric, thermally reversible dental astringent gel composed of an admixture containing substantially completely hydrolyzed polyvinyl alcohol of moderate molecular weight and moderate solution viscosity, polyhydroxy aromatic gelling agent, aluminum chloride and water to convert the gel to a sol, applying the sol at a tissue compatible temperature to gingival tissue, allowing the sol to cool and form a solid, tack-free, elastomeric gel, and removing the gel from the tissue.

PRIOR ART

It is disclosed in the DuPont brochure entitled "ELVANOL polyvinyl alcohol 71-30 Properties and Uses" under the heading "Gelling Agents and Precipitants" that reagents that gel polyvinyl alcohol solutions include (a) certain dyes and aromatic hydroxy compounds, which form thermally reversible gels, and (b) inorganic complexing agents which form thermally stable gels. The DuPont brochure, with reference to U.S. Pat. Nos. 2,249,536; 2,249,537; and 2,249,538 (McDowell et al., 1941) notes that organic compounds that have been reported to form thermally reversible gels include resorcinol, catechol, phloroglucinol salicylanilide, gallic acid and 2,4-dihydroxybenzoic acid. It is further pointed out in the DuPont brochure that the presence of some salts may not impair the stability of solutions of polyvinyl alcohol, even in substantial amounts, while other salts act as precipitants or gelling agents at low concentrations and, in this connection, it is disclosed that polyvalent metal salts and complexes insolubilize polyvinyl alcohol.

U.S. Pat. No. 2,408,377 (Dangelmajer, 1946) discloses that the addition of aluminum chloride to polyvinyl alcohol compositions containing glyceryl, formamide and water greatly increase their stability and increase the duration of their flexibility at elevated temperatures. This effect is referred to as "thermal stabilizing" and the means for effecting it as "thermal stabilizing agents." Thus, as characterized by the patentee, aluminum chloride is a thermal stabilizing agent for polyvinyl alcohol compositions. The patentee points out that the compositions are adapted to be molded into tubing, gaskets and the like for use in engines and machinery where sustained high temperatures are encountered.

U.S. Pat. No. 3,856,941 (Turner, 1974) discloses a spreadable astringent gel for application to the skin to effect tightening of sagging or loose skin which comprises an admixture of, for example, aluminum chloride, zinc sulfate, polyvinyl alcohol having a molecular weight between 10,000 and 96,000 and up to 13% acetyl groups, an emollient such as glyceryl, and water.

In contrast to the general observations regarding the insolubilizing, thermostabilizing and spreadability effects of polyvalent metal salts on polyvinyl alcohol, it has been discovered that aluminum chloride, a hemostatic dental astringent and a polyvalent metal salt, may be embodied in and is compatible with thermally reversible, elastomeric, polyvinyl alcohol gels which employ aromatic hydroxy compounds as the gelling agent. With respect to this compatibility, it has been found that the aluminum chloride neither insolubilizes the polyvinyl alcohol nor interferes with the gelling properties of the aromatic hydroxy gelling agents and, of equal significance, is the finding that neither polyvinyl alcohol nor the aromatic hydroxy gelling agents interferes with the hemostatic and astringent properties of aluminum chloride.

The results of this invention are attained when the polyvinyl alcohol is a substantially completely hydrolyzed composition have a moderate molecular weight and a moderate solution viscosity. As shown by certain of the examples hereinafter set forth, the results of this invention are not attained when the polyvinyl alcohol is a partially hydrolyzed composition having a low molecular weight and a low solution viscosity.

DETAILED DESCRIPTION

Composition

The thermally reversible gingival retraction gels of this invention are composed of an admixture comprising polyvinyl alcohol, hydroxy aromatic gelling agent, aluminum chloride and water.

It is essential to this invention that the polyvinyl alcohol be characterized by substantially complete hydrolysis, moderate molecular weight and moderate solution viscosity. The polyvinyl alcohol which meets these parameters has a mole percent hydrolysis of at least about 99, a molecular weight from about 120,000 to about 150,000, and is further characterized in that a 4 wt.% aqueous solution thereof at 20° C. has a viscosity from about 28 to about 32 centipoises as determined by the Hoeppler falling ball method. The mole percent hydrolysis is generally from about 99 to about 99.8, i.e. about 99 to about 99.8 hydroxyl groups per mole and about 0.2 to 1 acetyl group per mole. Polyvinyl alcohol is generally present in the gel in an amount from about 5 to about 25 wt.%, with an intermediate range being from about 10 to about 20 wt.%, and a preferred range being from about 15 to about 18 wt.%.

The gelling agents which can be used in the invention include polyhydroxy aromatic compounds such as 2,4-dihydroxybenzoic acid (beta-resorcyclic acid), and 3,4,5-trihydroxybenzoic acid (gallic acid), 1-methyl-3,5-dihydroxybenzene (orcinol), and 4-chloro-1,3-dihydroxybenzene (4-chlororesorcinol). A preferred gelling agent is gallic acid. The gelling agent is generally present in the gel in an amount from about 1.3 to about 6 wt.%, with an intermediate range being from about 2.5 to about 5 wt.%, and a preferred range being from about 3.3 to about 4.1 wt.%.

The hemostatic dental astringent which can be used in this invention is aluminum chloride, preferably, aluminum chloride hydrate as, for example, aluminum chloride hexahydrate. The aluminum chloride hemostatic astringent is generally present in the gel in an amount from about 2 to about 12 wt.%, with an intermediate range being from about 4 to about 11 wt.%, and a preferred range being from about 7 to about 10 wt.%.

Water is present in the gel in an amount to make up 100 wt.%.

The admixture may be formulated with a trace amount of a suitable dye or other coloring agent to impart a selected color to the gel.

METHOD OF PREPARATION

In one embodiment, the thermally reversible dental astringent gel is prepared by admixing and heating Composition A comprising an aqueous solution containing polyvinyl alcohol with Composition B comprising an aqueous system containing the gelling agent and the hemostatic dental astringent until a sample of the resulting admixture, upon cooling, forms a gel.

Composition A is advantageously prepared by blending a suitable coloring agent, if any, with granular polyvinyl alcohol and then adding the polyvinyl alcohol composition to water, with agitation, to form a cold slurry at a temperature of about 24° C. (75° F.) or below. This slurry is then heated with continued agitation to melt and dissolve the polyvinyl alcohol composition. Typically, the temperature of the cold slurry is raised to and maintained at 90°–95° C. (194°–203° F.) until the composition is dissolved. The heating and agitation step is preferably carried out in a vessel equipped with a steam jacket or steam coil.

The concentration of the polyvinyl alcohol in Composition A is generally from about 5 to about 25 wt.%, with an intermediate range being from about 10 to about 20 wt.%, and a preferred range being from about 15 to about 18 wt.%. The concentration of water in Composition A is generally from about 74 to about 50 wt.%, with an intermediate range being from about 68 to about 55 wt.% and a preferred range being from about 63 to about 59 wt.%. The concentration of the ingredients in Composition A, by wt.%, is based on the combined weights of Compositions A and B.

Composition B is prepared by adding aluminum chloride and polyhydroxy aromatic gelling agent to water with agitation.

Aluminum chloride is generally present in Composition B in an amount from about 2 to about 12 wt.%, with an intermediate range being from about 4 to about 11 wt.%, and a preferred range being from about 7 to about 10 wt.%. The polyhydroxy aromatic gelling is generally present in Composition B in an amount from about 1.3 to about 6 wt.%, with an intermediate range being from about 2.5 to about 5 wt.%, and a preferred range being from about 3.3 to about 4.1 wt.%. The amount of water in Composition B is generally in the range from about 18 to about 12 wt.%, with an intermediate range being from about 17 to about 14 wt.%, and a peferred range being from about 16 to about 15 wt.%. The concentration of the ingredients in Composition B, by wt.%, is based upon the combined weight of Compositions A and B.

Compositions A and B are admixed and heated until a sample of the resulting admixture, upon cooling, forms a gel. The admixing step is advantageously carried out at a temperature from about 90° to about 100° C. In a preferred aspect, Composition B is prepared by adding the dental astringent and the gelling agent to water and heating the resulting aqueous system at a temperature from about 90° to about 100° C. until the gelling agent dissolves, or alternatively, adding the astringent and gelling agent to heated water which is at a temperature from about 90° to about 100° C. to obtain a solution thereof. Composition B, while it is hot (in excess of about 90° C.) is advantageously added to Composition A at its solution temperature (90°–95° C.) with agitation and continued heating whereby a smooth admixing step is obtained.

In a preferred embodiment, the thermally reversible dental astringent gel is prepared by forming, with agitation, a cold aqueous slurry of polyvinyl alcohol alone or together with a suitable coloring agent. This slurry is then heated to and maintained at a temperature from about 76.6° C. (170° F.) to about 95° C. (203° F.), with continued agitation, until the polyvinyl alcohol composition is dissolved. The thermally reversible gelling agent is then added to the aqueous solution of polyvinyl alcohol followed by the addition of the hemostatic dental astringent, with continued agitation and heating in the aforesaid temperature range until these ingredients are dissolved in the aqueous system and a smooth admixture is obtained. The broad, intermediate and preferred concentration ranges for polyvinyl alcohol, the thermally reversible gelling agent, hemostatic dental astringent and water for use in this embodiment of the invention correspond to the concentration ranges for these ingredients set forth hereinabove under the heading Composition.

Upon completion of the admixing step, the hot liquid suspension or sol may be loaded into a syringe type vial in the manner described in U.S. Pat. No. 3,731,453 (Porteous, 1973) which discloses a method for preparing syringe type vials of thermally reversible, hydrocolloid impression material. The loaded syringe type vial is provided with a movable stopper at one end and the other end is equipped with a needle permeable cap. The hot sol, upon cooling to ambient temperature, forms a gel in the vial. In this connection, the sol becomes very thick at about 54.4° C. (130° F.) and forms a solid, tack-free, elastomeric gel at about 43.3° C. (110° F.).

METHOD OF USE

To prepare the hemostatic/astringent gel for application to gingival tissue, the vial containing the solid, elastomeric gel may be heated in boiling water for about 2 to about 20 minutes to convert the gel to a sol and then placed in a storage bath at about 65.5° C. (150° F.) where it will remain liquid for about two weeks preparatory to use. Alternatively, the vial containing the gel may be heated in a water bath at about 65.5° C. for at least about 10 minutes to convert it to a sol for use.

The vial containing the hemostatic/astringent sol at about 65.5° C. is inserted into a suitable syringe and a hollow needle device is attached to the syringe with one end of the needle penetrating the needle permeable cap. The sol is advantageously formulated so that it will solidify to a solid, elastomeric gel in about 4 minutes after it is removed from 65.5° C. water bath. This solidification time provides about 1 minute working time for application of the sol to the tissue and about 3 minutes set time on the tissue. Within this time frame, the sol may be applied to the tissue at a temperature from about 60° to 63° C. (140°–145° F.).

The sol may be used in conjunction with a gingival retraction cord by placing the cord in the gingival sulcus and applying the sol to the top of the cord to help seal the sulcus and aid in hemostasis. The sol may also be used after electrosurgery or gingival curretage by applying the sol around the prepared teeth to aid in hemostasis.

EXAMPLES

The following examples further illustrate the invention.

Polyvinyl alcohol used in Example I & II was obtained from DuPont under the designation Elvanol 71-30. This polyvinyl alcohol had the following typical properties as set forth in the supplier's technical brochure.

| Form | granular |
| --- | --- |
| Color | white |
| Hydrolysis, mole % | 99.0–99.8 |
| Saponification number | 3–12 |
| Viscosity, cp (mPa.s) (4% aq. soln., Hoeppler method) | 28–32 |
| Bulk density, lb./cu.ft. | 25–27 |
| Specific gravity | 1.30 |
| Resin density, lb./gal. | 10.8 |

EXAMPLE I

This example illustrates the preparation of thermally reversible, hemostatic/astringent gels by the addition of a polyhydroxy aromatic gelling agent and hemostatic dental astringent to an aqueous polyvinyl alcohol solution.

In runs 1(a) through 1(g), Composition B was prepared by dispersing, with agitation, aluminum chloride hydrate and gallic acid in water; and Composition A was prepared by forming, with agitation, a cold slurry of polyvinyl alcohol and water and heating the cold slurry with steam heat to a temperature in excess of about 90° C. until the polyvinyl alcohol melted and dissolved in the water to form a relatively viscous solution. Upon completion of the PVA dissolving step, heat was withdrawn and Composition B was added thereto, with mixing. Steam heat was then reapplied and the admixture was heated, with continued agitation, until a sample thereof, upon cooling, formed a gel. The concentration of the ingredients in runs 1(a) through 1(g) is set forth in Table I as well as original batch set time and the weight percent of aluminum chloride and gallic acid based on the weight of PVA.

TABLE I

| | wt., grams | | | | | | |
| --- | --- | --- | --- | --- | --- | --- | --- |
| | 1 (a) | 1 (b) | 1 (c) | 1 (d) | 1 (e) | 1 (f) | 1 (g) |
| Composition B | | | | | | | |
| Aluminum chloride | 2.0 | 2.0 | 3.4 | 136 | 13.6 | 13.60 | 13.6 |
| Gallic acid | 1.4 | 1.7 | 1.7 | 68 | 8.3 | 9.66 | 11.0 |
| Water | 12.5 | 13.0 | 13.0 | 520 | 52.0 | 52.00 | 52.0 |
| Composition A | | | | | | | |
| Polyvinyl alcohol | 13.75 | 13.75 | 13.75 | 552 | 55.2 | 55.2 | 55.2 |
| Water | 50.00 | 50.00 | 50.00 | 2000 | 200 | 200 | 200 |
| Set time, min. (orig. batch) | 2–3 | 1–2 | | | 4.5 | 3.5 | 2.5 |
| AlCl$_3$, % of PVA | 14.5 | 14.5 | 24.7 | 24.6 | 24.6 | 24.6 | 24.6 |
| Gallic acid, % of PVA | .10 | 12.4 | 12.4 | 12.3 | 15.0 | 17.5 | 20.00 |

The addition of the aqueous dispersion of aluminum chloride hydrate and gallic acid to the hot aqueous PVA solution resulted in curdling and clumping which merged into a uniform dispersion when the temperature of the admixture reached 90° C. Also, as shown by Table I, the set time of the thermally reversible gel is reduced by increasing the concentration of the gelling agent with respect to the net weight of the polyvinyl alcohol.

EXAMPLE II

This example illustrates a method for preparing thermally reversible, hemostatic/astringent gels which avoids curdling and clumping in the admixing step.

In runs 2(a) and 2(b), Composition B was prepared by heating, with agitation, aluminum chloride hydrate, gallic acid and water to the boiling point thereof and maintaining this mixture at the boiling point until the gallic acid dissolved. Composition A was prepared by blending the dye into the granular polyvinyl alcohol and adding the blended mixture to cool water, with agitation, to form a cold slurry. The cold slurry was agitated and heated with steam heat to a temperature in excess of about 90° C. until the polyvinyl alcohol/dye mixture dissolved. Composition B, which was at a temperature above 90° C., was added to Composition A, which was also at a temperature above 90° C., and steam heating and agitation were continued at a temperature above 90° C. until a sample of the admixture, upon cooling, formed a gel.

The concentration of the ingredients in runs 2(a) and 2(b), set time and the weight percent of aluminum chloride and gallic acid based on the net weight of polyvinyl alcohol are set forth in Table II

TABLE II

|  | Weight, grams | |
|---|---|---|
|  | 2(a) | 2(b) |
| Composition B |  |  |
| Aluminum chloride | 13.6 | 102 |
| Gallic acid | 12.4 | 93 |
| Water | 52.0 | 400 |
| Composition A |  |  |
| Polyvinyl alcohol | 55.2 | 414.0 |
| Palio Fast Green | 0.0 | 1.5 |
| Water | 200.0 | 1600.0 |
| Set time, sec.(orig.batch) | 45 |  |
| AlCl$_3$, % of PVA | 24.6 | 24.6 |
| Gallic acid, % of PVA | 22.4 | 22.4 |

The intermixing of the hot solutions of Compositions A and B resulted in a smooth admixing step without clumping or curdling. Run 2(b) was repeated except that the aluminum chloride hydrate and gallic acid were added to and dissolved in boiling water, with agitation. This alternative procedure also resulted in a smooth admixing step without curdling or clumping.

The hot fluid dispersion from run 2(b) was loaded into 1.8 cc syringe vials where the fluid, upon cooling to ambient temperature, formed a gel. This gel was evaluated for thermal reversible characteristics with respect to fluidizing temperature, working time and set time. It was found that the vial could be placed in boiling water for about 2 to about 20 minutes to convert the gel to a sol and then placed in a storage bath at about 65.5° C. (150° F.) where the sol would remain liquid for about two weeks preparatory to use; or the vial could be heated in a water bath at about 65.5° C. for at least about 10 minutes to convert the gel to a sol for use. Upon removal of the vial from the water bath at 65.5° C., the sol had an overall set time of about 4 minutes which allows about 1 minute working time for application to the tissue and about 3 minutes set time on the tissue. The thermally reversible gel was evaluated by a clinical investigator and found to be an effective hemostatic dental astringent.

EXAMPLE III

This example demonstrates that the use of a substantially completely hydrolyzed polyvinyl alcohol having a moderate molecular weight and a moderate solution viscosity is essential to the achievement of the results of this invention, namely, the production of a thermally reversible, solid, tack-free, elastomeric, dental astringent gel.

A series of runs were carried out to evaluate different polyvinyl alcohol compositions in the following basic formula:

| Composition | Wt., grams |
|---|---|
| Water | 70.012 |
| Color | 0.018 |
| Polyvinyl alcohol | 16.650 |
| Gallic acid | 3.320 |
| Aluminum chloride (6H$_2$O) | 10.000 |
|  | 100.000 |

The procedure employed in the preparation and evaluation of the composition for each run was as follows: a dry blend of the color and the polyvinyl alcohol was added to cold water with agitation to form a slurry which was then heated to 170° F. for the purpose of dissolving the blend; gallic acid and aluminum chloride hexahydrate were sequentially added to the fluid material with continued heating and agitation for the purpose of dissolving these ingredients in the fluid system; the resulting composition was added to 1.8 cc syringe vials which were capped and cooled to ambient temperature; the vials were then heated in boiling water for 10 minutes, stored for one hour at 150° F., and placed in a metal syringe for extrusion through an attached 19 gauge blunt needle into a typodon.

Run No. 1

The polyvinyl alcohol used in this run (DuPont EL-VANOL 70-31) had a mole percent hydrolysis from 99 to 99.8, a molecular weight from 120,000 to 150,000 and a 4 wt.% water solution viscosity at 20° C. from 28 to 32 centipoises as determined by the Hoeppler falling ball method. The polyvinyl alcohol blend, gallic acid and aluminum chloride readily dissolved in the heated water to form a liquid composition which was loaded into the syringe vials. Upon cooling the vials to ambient temperature, the liquid composition was transformed into a solid, non-spreadable, elastomeric gel. When the vials were heated in boiling water, the solid, elastomeric gel was converted into a liquid composition which maintained its liquidity when stored at 150° F. The warm liquid was readily and easily extruded through the syringe needle and within one to two minutes following extrusion formed a solid, tack-free, elastomeric gel.

Run No. 2

The polyvinyl alcohol used in this run (DuPont EL-VANOL 70-05) had a mole percent hydrolysis from 99 to 99.8, a molecular weight from 25,000 to 35,000 and a 4 wt.% water solution viscosity at 20° C. from four to six centipoises as determined by the Hoeppler falling ball method.

Run No. 3

The polyvinyl alcohol used in this run (DuPont EL-VANOL 51-05) had a mole percent hydrolysis from 87 to 89, a molecular weight from 25,000 to 35,000 and a 4 wt.% water solution viscosity at 20° C. from four to six centipoises as determined by the Hoeppler falling ball method.

Run No. 4

The polyvinyl alcohol used in this run (Monsanto GELVATOL 20-30) had a mole percent hydrolysis from 87 to 89, a low molecular weight and a low solution viscosity.

In Runs 2, 3 and 4, there was extensive foaming during the heating of the cold water slurry of the blend of polyvinyl alcohol and color together with percipitation of a significant amount of the polyvinyl alcohol. Upon the addition of gallic acid in each of these runs, there was further percipitation of the polyvinyl alcohol which did not solubilize with additional heating. The aluminum chloride hexahydrate which was added in each Run went into solution. Each of the resulting fluid layers in Runs 2, 3 and 4 was a highly viscous, tacky material with extensive foam throughout the fluid. This material was loaded, with great difficulty, into the syringe vials which were allowed to cool to ambient temperature. The cooling of the material did not produce any change in the physical characteristics of the viscous fluid and, in particular, did not transform the fluid into a solid, tack-free, elastomeric gel. The vials were heated in boiling water for ten minutes and stored at 150° F. for one hour with no discernible change in the physical characteristics of the viscous fluid. This material could not be extruded through the syringe needle and several attempts to do so resulted in broken vials.

EXAMPLE IV

This example demonstrates that the composition and method described in U.S. Pat. No. 3,856,941 (Turner, 1974) does not produce a thermally reversible, solid, tack-free, elastomeric, dental astringent gel.

Following the procedure described in Example I of the Turner patent, 10 grams of aluminum chloride, 5 grams of alum and 5 grams of zinc sulfate were dissolved in 60 grams of water while heating to 50° C. with stirring. 40 cc of 2 N sodium hydroxide solution were added slowly thereto to adjust the pH of the solution to 3.5. Three grams of polyvinyl alcohol having a molecular weight between 10,000 and 96,000 and a mole percent hydrolysis of 87 (13% acetate groups) were dissolved in the solution with continued heating at 50° C. and stirring. The resulting solution was diluted with water to 100 ml. This solution was further diluted with 15 ml of water while stirring and the resulting composition was allowed to stand at room temperature. There was obtained a pourable, viscous fluid having a fluidity similar to the fluidity of maple syrup.

The viscous fluid was added to syringe vials which were heated in boiling water for ten minutes and stored for one hour at 150° F. There was no discernible difference in the fluidity of the product as a result of the heating and storage steps. Each warm vial was placed in a syringe and extruded through a 19 gauge blunt needle into a typodon. The extruded material, upon standing, remained fluid and, in particular, did not form a solid, tack-free, elastomeric gel.

In view of the foregoing description and examples, it will become apparent to those of ordinary skill in the art that equivalent modifications thereof may be made without departing from the spirit and scope of this invention.

That which is claimed is:

1. A solid, tack-free, elastomeric, thermally reversible dental astringent gel composed of an admixture comprising:
   (a) polyvinyl alcohol in an amount from about 5 to about 25 wt.%, said polyvinyl alcohol having a mole percent hydrolysis of at least about 99, a molecular weight from about 120,000 to about 150,000 and a 4 wt.% water solution viscosity at 20° C. from about 28 to about 32 centipoises as determined by the Hoeppler falling ball method,
   (b) aluminum chloride in an amount from about 2 to about 12 wt.%,
   (c) polyhydroxy aromatic gelling agent in an amount from about 1.3 to about 6 wt.%, and
   (d) water to 100 wt.%.

2. The thermally reversible gel of claim 1 wherein polyvinyl alcohol is present in an amount from about 10 to about 20 wt.%, the aluminum chloride is present in an amount from about 4 to about 11 wt.%, and the polyhydroxy aromatic gelling agent is present in an amount from about 2.5 to about 5 wt.%.

3. The thermally reversible gel of claim 1 wherein the gelling agent is 2,4-dihydroxybenzoic acid.

4. The thermally reversible gel of claim 1 wherein the gelling agent is 3,4,5-trihydroxybenzoic acid.

5. The thermally reversible gel of claim 1 wherein the gelling agent is 1-methyl-3,5-dihydroxy benzene.

6. The thermally reversible gel of claim 1 wherein the gelling agent is 4-chloro-1,3-dihydroxy benzene.

7. The thermally reversible gel of claim 1 wherein polyvinyl alcohol is present in an amount from about 15 to about 18 wt.%, aluminum chloride is present in an amount from about 7 to about 10 wt.%, and the polyhydroxy aromatic gelling agent is present in an amount from about 3.3 to about 4.1 wt.%.

8. A method for preparing a solid, tack-free, elastomeric, dental astringent gel which comprises:
   admixing and heating at a temperature from about 76° to about 95° C. a fluid system containing
   (a) polyvinyl alcohol in an amount from about 5 to about 25 wt.%, said polyvinyl alcohol having a mole percent hydrolysis of at least about 99, a molecular weight from about 120,000 to about 150,000 and a 4 wt.% water solution viscosity at 20° C. from about 28 to about 32 centipoises as determined by the Hoeppler falling ball method,
   (b) aluminum chloride in an amount from about 2 to about 12 wt.%,
   (c) polyhydroxy aromatic gelling agent in an amount from about 1.3 to about 6 wt.%, and
   (d) water to 100 wt.%,
   until a sample thereof, upon cooling, forms a solid, tack-free, elastomeric gel.

9. The method of claim 8 wherein polyvinyl alcohol is present in an amount from about 10 to about 20 wt.%, the aluminum chloride is present in an amount from about 4 to about 11 wt.%, and the polyhydroxy aromatic gelling agent is present in an amount from about 2.5 to about 5 wt.%.

10. The method of claim 8 wherein polyvinyl alcohol is present in an amount from about 15 to about 18 wt.%, aluminum chloride is present in an amount from about 7 to about 10 wt.%, and the polyhydroxy aromatic gelling agent is present in an amount from about 3.3 to about 4.1 wt.%.

11. The method of claim 8 wherein the gelling agent is 2,4-dihydroxybenzoic acid.

12. The method of claim 8 wherein the gelling agent is 3,4,5-trihydroxybenzoic acid.

13. The method of claim 8 wherein the gelling agent is 1-methyl-3,5-dihydroxy benzene.

14. The method of claim 8 wherein the gelling agent is 4-chloro-1,3-dihydroxy benzene.

15. A method for constricting and retracting gingival tissue which comprises heating a solid, tack-free, elastomeric, thermally reversible dental astringent gel composed of an admixture containing (a) about 5 to about 25 wt.% polyvinyl alcohol, said polyvinyl alcohol having a mole percent hydrolysis of at least about 99, a molecular weight from about 120,000 to about 150,000 and a 4 wt.% water solution viscosity at 20° C. from about 28 to about 32 centipoises as determined by the Hoeppler falling ball method, (b) about 2 to about 12 wt.% aluminum chloride, (c) about 1.3 to about 6 wt.% polyhydroxy aromatic gelling agent and (d) water to 100 wt.% to obtain a sol,
   applying the sol at a tissue compatible temperature to gingival tissue,
   allowing the sol to cool and form a solid, tack-free, elastomeric gel; and
   removing the gel from the tissue.

16. The method of claim 15 wherein the thermally reversible gel contains about 10 to about 20 wt.% polyvinyl alcohol, about 4 to about 11 wt.% aluminum chloride and about 2.5 to about 5. wt.% polyhydroxy aromatic gelling agent.

17. The method of claim 15 wherein the thermally reversible gel contains about 15 to about 18 wt.% polyvinyl alcohol, about 7 to about 10 aluminum chloride and about 3.3 to about 4.1 wt.% polyhydroxy aromatic gelling agent.

18. The method of claim 15 wherein the gelling agent is 2,4-dihydroxybenzoic acid.

19. The method of claim 15 wherein the gelling agent is 3,4,5-trihydroxybenzoic acid.

20. The method of claim 15 wherein the gelling agent is 1-methyl-3,5-dihydroxy benzene.

21. The method of claim 15 wherein the gelling agent is 4-chloro-1,3-dihydroxy benzene.

* * * * *